United States Patent [19]

Trotz et al.

[11] Patent Number: 4,533,736
[45] Date of Patent: Aug. 6, 1985

[54] PROCESS FOR THE PREVENTION OR REDUCTION OF DISCOLORATION OF SODIUM PYRITHIONE

[75] Inventors: Samuel I. Trotz, Orange; Douglas A. Farmer, Jr., Madison, both of Conn.

[73] Assignee: Olin Corporation, Cheshire, Conn.

[21] Appl. No.: 626,951

[22] Filed: Jul. 2, 1984

Related U.S. Application Data

[62] Division of Ser. No. 352,813, Feb. 26, 1982, Pat. No. 4,482,715.

[51] Int. Cl.³ .................... A61K 31/44; C07D 213/89
[52] U.S. Cl. ......................................... 546/290; 546/6
[58] Field of Search .................... 546/6, 290; 424/245; 514/345

[56] References Cited

U.S. PATENT DOCUMENTS 2,809,971 10/1957 Bernstein et al. .................... 260/270
3,058,997 10/1962 Taylor et al. ........................ 549/250
4,161,526 7/1979 Gorman .............................. 424/245

OTHER PUBLICATIONS

Standard ASTM Test D1544-80.
Olin Product Data sheets for Zinc Omadine ® and Sodium Omadine ®.
Merck et al., 9th Ed., 1976, pp. 627, 1110, and 1121.

Primary Examiner—Henry R. Jiles
Assistant Examiner—J. G. Mullins
Attorney, Agent, or Firm—William A. Simons; Thomas P. O'Day

[57] ABSTRACT

Disclosed is a process for producing a zinc pyrithione product having an acceptable white or off-white color and preventing or reducing discoloration of sodium pyrithione solutions by treating said sodium pyrithione solutions (which are precursors to zinc pyrithione) with an effective amount of a selected reducing agent to prevent or reduce the discoloration, said reducing agent selected from the class consisting of alkali metal sulfites, alkali metal bisulfites, hydrazine, and mixtures thereof.

6 Claims, No Drawings

PROCESS FOR THE PREVENTION OR REDUCTION OF DISCOLORATION OF SODIUM PYRITHIONE

This is a division of application Ser. No. 352,813, filed Feb. 26, 1982, now U.S. Pat. No. 4,482,715.

BACKGROUND OF THE INVENTION

1. Field of the Invention

The present invention relates to a process for prevention or reduction of discoloration of sodium or zinc pyrithione.

2. Description of the Prior Art

Zinc pyrithione [also known as zinc pyridine-2-thiol-N-oxide or bis[1-hydroxy-2(H) pyridinethionato]-zinc] is an excellent biocide. It has been employed as a broad-spectrum antimicrobial agent and preservative in metal working fluids, plastics, and cosmetics. Its principal uses are as an antidandruff agent in hair products or as a preservative in various cosmetics and toiletries. Sodium pyrithione [also called the sodium salt of 1-hydroxy-2-pyridinethione, sodium pyridine-2-thiol-N-oxide, or 2-pyridinethiol-1-oxide, Na salt] is also employed as a preservative in various cosmetics and toiletries.

Zinc pyrithione may be made by reacting 1-hydroxy-2-pyridinethione or a soluble salt thereof with a zinc salt (e.g., $ZnSO_4$) to form a zinc pyrithione precipitate. See U.S. Pat. No. 2,809,971, which issued to Bernstein and Losee on Oct. 15, 1957. Generally, the sodium pyrithione is employed as the precursor of zinc pyrithione.

Since the esthetics of cosmetics and toiletries normally require certain desirable colors, and the formulators of such products go to great lengths to achieve specific color effects, any ingredient which varies very much from white or colorless may make the colorant formulators' task very difficult.

Sodium pyrithione and zinc pyrithione products occasionally have problems with meeting such strict color specifications. It is believed that such discoloration results from the oxidation of unwanted traces of contaminants during processing of the sodium pyrithione solutions. One method of removing these contaminants is to carry out multi-step purification processes with such solutions. This is costly and adds extra processing steps. Accordingly, there is a need for a better method of preventing or removing discoloration of sodium or zinc pyrithione.

BRIEF SUMMARY OF THE INVENTION

The present invention, therefore, is directed to a process for preventing or reducing discoloration of aqueous sodium pyrithione solutions by treating the sodium pyrithione solution with an effective amount of a selected reducing agent to prevent or reduce the discoloration. The present invention is also directed to a process for producing a zinc pyrithione product having an acceptable white or off-white color by reacting said sodium pyrithione, after the above treatment, with a zinc salt to form the zinc pyrithione product. The reducing agents of the present invention are selected from the class consisting of alkali metal sulfites, alkali metal bisulfites, hydrazine, and mixtures thereof.

DETAILED DESCRIPTION

The sodium pyrithione reactant for the present invention is a well-known commercial product and is commonly made by reacting 2-chloropyridine-N-oxide with NaSH and NaOH. See U.S. Pat. No. 3,159,640, which issued to McClure on Dec. 1, 1964.

The other reactant for making zinc pyrithione is, namely, a zinc salt. Any suitable zinc salt which is soluble in an aqueous solution of sodium pyrithione may be used. The preferred are $ZnCl_2$, $ZnSO_4$, and hydrates thereof. $ZnSO_4$ is the most preferred.

According to a preferred aspect of the process of the present invention, an aqueous solution of sodium pyrithione is mixed with one or more of the above-noted reducing agents. The sodium pyrithione content of this aqueous solution may range up to about 50% by weight. The amount of reducing agent or agents employed may be any amount which is effective to prevent or reduce discoloration of sodium or zinc pyrithione. The expression "effective amount to prevent or reduce discoloration" may vary and is dependent upon several parameters including the temperature and time of processing; quality of sodium pyrithione and zinc salt reactants; type of reaction vessel; and the like. The amount of reducing agent employed will preferably be from about 2.5% to about 10% on a mole basis of sodium pyrithione reactant.

Not all reducing agents are suitable for the process of this invention. For example, phosphites are not suitable because they form precipitates with zinc which would contaminate the desired product. Also, reducing agents like $Na_2S_2O_3$ and $NaNO_2$ that do not form precipitating complexes with the reactants were surprisingly found to have little effect on preventing or reducing discoloration. It should also be noted that alkali metal sulfites (e.g., $Na_2SO_3$) go partially to the bisulfite form at the pH's involved in the present reaction. This is due to acid-base equilibrium.

The term "discoloration" as employed herein with sodium pyrithione solutions may mean any unacceptable dark brown color other than a light amber to yellow or tan color. The latter are generally suitable for giving acceptable zinc pyrithione or sodium pyrithione end products. One way of quantitatively measuring for discoloration in sodium pyrithione is by measuring the Gardner-Hellige Varnish Color values (note Examples below).

The term "discoloration" as employed herein with zinc pyrithione may mean any unacceptable gray, green, red, yellow, blue, brown, or color other than a white or off-white color. The latter are generally suitable in most hair products, cosmetic, and toiletry applications. One way of quantitatively measuring for discoloration in zinc pyrithione is by measuring the Hunter color parameters and calculating a whiteness value from them (note Examples below). It should be noted that the causes of discoloration in sodium pyrithione solutions and zinc pyrithione made from the former are not clearly known. It is believed one possible cause is oxidation of contaiminants during further processing of sodium pyrithione.

After the reducing agent is mixed with the sodium pyrithione, the reaction vessel may be heated to an elevated reaction temperature to effect the reaction with the zinc salt. The zinc salt is then added to the mixture, whereby zinc pyrithione would precipitate from the solution.

The preferred reaction temperature is from about 20° C. to about 100° C.; more preferably from about 60° C. to about 95° C. The processing time will vary with the reaction temperature (e.g., from about 10 minutes to about 120 minutes).

The amount of zinc salt added should preferably be stoichiometrically sufficient so that the sodium pyrithione is completely reacted. The preferable mole ratios of zinc salt to sodium pyrithione may range from about 0.9:2 to about 1.25:2; more preferably from about 1:2 to about 1.1:2.

When the reaction is complete, the formed zinc pyrithione will precipitate from the solution. This precipitate may be filtered from the reaction mixture and further processed according to conventional means.

The following Examples and Comparisons are illustrative of preferred embodiments of the present invention. All parts and percentages are by weight unless explicitly stated otherwise.

EXAMPLE 1

An aqueous solution of unpurified sodium pyrithione (13% by weight, 390.2 grams solution, 0.34 moles of active compound) containing 5.1 grams of a surfactant was charged into a 1000 ml round bottom flask equipped with stirrer, thermometer, heating mantle and addition funnel. The Gardner-Hellige Varnish Color Scale[1] reading of this solution was 10.

[1]Measured according to ASTM D1544-80 [Color of Transparent Liquids (Gardner Color Scale)].

Solid sodium bisulfite (3.6 grams, 0.034 mole) was then added to the flask at ambient temperature (about 20°–25° C.). The Gardner-Hellige Varnish Color reading was then measured to be 8. The solution was heated up to 95° C. during a period of 20 minutes. The solution appeared to darken slightly after this heating.

An aqueous solution of $ZnSO_4$ (9.7% by weight $ZnSO_4$, 270.0 grams, 0.163 moles $ZnSO_4$) was added to the heated flask through the addition funnel. A precipitate made up of substantially zinc pyrithione was formed. This precipitate was removed from the reaction mixture by filtration.

The Hunter color[2] values of this filter cake were measured to be as L=94.5, a=−5.4, and b=6.0. Calculated whiteness[3] from these Hunter color values was 56.5 (as compared to MgO=100).

[2]Measured on a Hunterlab Color/Difference Meter D25D2 manufactured by Hunter Associates Laboratory Inc. of Fairfax, Va., according to AATCC test method 110-1972.
[3]Whiteness=$0.01L^2-0.057bL$

COMPARISON 1

The procedure of Example 1 was followed except no $NaHSO_3$ was added to the sodium pyrithione solution. The solution darkened considerably during heating to 95° C. The Hunter color values of the filter cake were L=90.1, a=−5.8, and b=11.4. Calculated whiteness was 21.8.

Comparing the whiteness values of Example 1 to Comparison 1, it can be readily seen that the addition of $NaHSO_3$ greatly improves the whiteness of the zinc pyrithione product.

EXAMPLES 2-7 AND COMPARISON 2

The abilities of different levels of sodium bisulfite to retard the discoloration of various aqueous solutions of unpurified sodium pyrithione were investigated. In this testing, the Gardner-Hellige Varnish Color values were measured both before addition of certain amounts of sodium bisulfite at room temperature (20°–25° C.) and after addition. These color values were again measured after heating the sodium pyrithione/sodium bisulfite mixture to 95°–100° C. for 15 minutes. The results are shown in the following Table I.

TABLE I

| Example (E) or Comparison (C) | Mole % $NaHSO_3$ Based on Sodium Pyrithione Moles | Color Prior to Addition | Color After Addition | Color After Heating |
| --- | --- | --- | --- | --- |
| E2 | 5.0 | 8.0 | 7.5 | 8.5 |
| E3 | 2.5 | 8.0 | 8.0 | 9.0 |
| E4 | 2.5 | 12.0 | 11.5 | 12.5 |
| E5 | 2.5 | 16.5 | 16.5 | 16.5 |
| E6 | 2.5 | 14.5 | 13.5 | 13.5 |
| E7 | 2.5 | 12.5 | 12.5 | 13.0 |
| E8 | 2.5 | 14.5 | 14.0 | 13.5 |
| C2 | 0 | 8.0 | — | 12.5 |

These results show even 2.5 mole % addition of $NaHSO_3$ will substantially eliminate discoloration during heating and may even improve the color of sodium pyrithione solutions at room temperatures.

EXAMPLES 8-9 AND COMPARISONS 3-6

For each of these runs, an aqueous solution of sodium pyrithione (279.8 grams solution, 9.6% active agent) was mixed with various reducing agents and 2.5 grams of a surfactant. In this testing, the Gardner-Hellige Varnish Color tests were taken after mixing at room temperature (25° C.). This mixture was heated to 95° C. and the Gardner-Hellige colors were again measured. Then, aqueous solutions of $ZnSO_4$ (152.1 gram solution by weight, 9.73% $ZnSO_4$) containing 1.52% by weight of a surfactant were added to the heated mixtures and zinc pyrithione precipitated from the reaction mixtures. The precipitates were filtered out and the filter cakes were washed with 1.5 liters of $H_2O$. A small sample of each product was measured for the Hunter color and calculated whiteness. The results of these runs are given in Table II, below.

TABLE II

| Example (E) or Comparison (C) | Reducing Agent Added | Wt. of Reducing Agent | Mole % of Reducing Agent | Gardner Color @ 25° C. | Gardner Color @ 95° C. | Hunter Colors L | Hunter Colors a | Hunter Colors b | Calculated Whiteness |
| --- | --- | --- | --- | --- | --- | --- | --- | --- | --- |
| C-3 | None | — | — | 7.0 | 8.5 | 91.1 | −7.2 | 14.8 | 5.0 |
| E-8 | $Na_2SO_3$ | 1.2 g | 5% | 6.5 | 6.5 | 94.2 | −7.1 | 9.8 | 35.1 |
| C-4 | $Na_2S_2O_3$ | 2.3 g | 8% | 7.5 | 9.5 | 91.6 | −7.5 | 14.9 | 4.9 |
| C-5 | $NaNO_2$ | 0.6 g | 5% | 7.5 | 9.5 | 90.8 | −7.0 | 15.9 | −1.3 |
| C-6 | $NaBH_4$ | 0.4 g | 6% | 7.0 | 7.5 | 93.0 | −7.4 | 13.6 | 12.1 |
| E-9 | 85% aqueous solution of $N_2H_4.H_2O$ | 0.5 g | 3% | 7.0 | 7.0 | 93.8 | −7.4 | 12.4 | 20.7 |

As can be seen from this data in Table II, both $Na_2SO_3$ and $N_2H_4.H_2O$ act as good reducing agents for preventing or reducing discoloration in zinc pyrithione product. $NaBH_4$ was marginal and $Na_2S_2O_3$ and $NaNO_2$ were surprisingly non-effective. These data indicate that not all reducing agents are effective for preventing or reducing discoloration in zinc pyrithione.

What is claimed is:

1. A process for preventing or reducing discoloration of aqueous sodium pyrithione solutions comprising
treating a sodium pyrithione solution with an effective amount of a selected reducing agent to prevent or reduce the discoloration, said reducing agent selected from the class consisting of alkali metal sulfites, alkali metal bisulfites, hydrazine, and mixtures thereof.

2. The process of claim 1 wherein said reducing agent is an alkali metal sulfite.

3. The process of claim 2 wherein said alkali metal sulfite is sodium sulfite.

4. The process of claim 1 wherein said reducing agent is an alkali metal bisulfite.

5. The process of claim 4 wherein said alkali metal bisulfite is sodium bisulfite.

6. The process of claim 1 wherein said sodium pyrithione is made by reacting 2-chloropyridine-N-oxide with NaSH and NaOH.

* * * * *